United States Patent [19]

Haus

[11] Patent Number: 4,677,117

[45] Date of Patent: Jun. 30, 1987

[54] STABILIZED PESTICIDAL COMPOSITIONS

[75] Inventor: Joseph B. Haus, Montclair, N.J.

[73] Assignee: Roussel Uclaf, Paris, France

[21] Appl. No.: 833,955

[22] Filed: Feb. 27, 1986

Related U.S. Application Data

[63] Continuation of Ser. No. 392,986, Jun. 28, 1982, abandoned.

[51] Int. Cl.[4] ............................................. A01N 43/08
[52] U.S. Cl. ..................................... 514/461; 514/972
[58] Field of Search ................................ 514/461, 972

[56] References Cited

U.S. PATENT DOCUMENTS

| | | |
|---|---|---|
| 3,465,007 | 9/1969 | Elliott ................................. 549/497 |
| 3,542,928 | 11/1970 | Elliott ................................. 514/461 |
| 3,671,630 | 6/1972 | Carroll et al. ....................... 514/166 |

*Primary Examiner*—Albert T. Meyers
*Assistant Examiner*—John M. Kilcoyne
*Attorney, Agent, or Firm*—Bierman & Muserlian

[57] ABSTRACT

The present invention provides stabilized oil-based pesticidal compositions in which (5-Benzyl-3-furyl)methyl 2,2-dimethyl-3-(2-methylpropenyl)cyclopropanecarboxylate may be used as the sole active ingredient or in combination with other pesticidal agents without the development of the unpleasant odor characteristic of that compound.

5 Claims, No Drawings

STABILIZED PESTICIDAL COMPOSITIONS

PRIOR APPLICATION

This application is a continuation of copending application Ser. No. 392,986 filed June 28, 1982, now abandoned.

SUMMARY OF THE INVENTION

The present invention relates to stabilized pesticidal compositions. In particular, the present invention relates to substantially odor-free, oil-based pesticidal compositions comprising in combination, a pesticidal component having as the active pesticidal agent (5-Benzyl-3-furyl)methyl 2,2-dimethyl-3-(2-methylpropenyl)cyclopropanecarboxylate, and a stabilizing component comprising at least one stabilizing compound selected from the group consisting of linolenic acid oils, tall oils and tung oils having conjugated double bonds, wherein the proportion of said stabilizing component present is at least two (2) times the proportion of the pesticidal agent.

BACKGROUND OF THE PRESENT INVENTION

The compound (5-Benzyl-3-furyl)methyl 2,2-dimethyl-3-(2-methylpropenyl)cyclopropanecarboxylate which is sometimes written as 5-benzyl-3-furylmethyl chrysanthemate, is more generally known by the generic term Resmethrin. (Either formula name or this generic term may be used interchangeably throughout this specification). This compound is a widely used, broad spectrum insecticide which combines a high insecticidal activity and low mammalian toxicity.

The compound, however, has one significant drawback which has limited its use. The compound is known to give off an unpleasant, urine-like odor after its application. In addition, the oder which is produced is very persistent and remains noticeable for a long period of time, particularly if the compound is used on absorptive surfaces such as rugs, wood paneling or the like.

Conventional odor control methods have been employed to attempt to mask this unpleasant odor. In this regard, perfumed masking agents have been tested, but the masking effect only lasts for a short period of time. The unpleasant odor of Resmethrin typically persists for such a long period of time that any masking effect of such a perfume becomes ineffective.

This unpleasant odor is readily detected after exposure to sunlight, or even bright artificial light. Antioxidants, ultraviolet screening sunscreens, oxidizing and reducing agents have been suggested to prevent light-induced decomposition. Some of these agents have been successful in delaying the on-set of the typical unpleasant, urine-like odor. In this regard, British Specification No. 1,429,437 shows the addition of 2,2'-methylene bis-(6-tert-butyl-4-ethylphenol), known to be an antioxidant, to render the odor of Resmethrin less unpleasant. Also disclosed as optional UV-absorbers were 4-tert-butylphenyl salicylate or 2-hydroxy-4-methoxybenzophenone.

The unpleasantness and persistance of this odor has limited the specific uses for which Resmethrin is generally acceptable. Further, these problems have limited the use of Resmethrin in general purpose insecticidal compositions. Such compositions typically contain two or more specific purpose insecticides in combination. For example, such compositions frequently contain synthetic pyrethroids, variously known as Allethrin (the allyl homolog of cinerin I available commercially from Rousell-Uclaf), Bioallethrin (d-transallethrin available commercially from Fairfield American Corp.), Neopynamin (tetramethrin commercially available from Sumitomo), or other pyrethrins, all of which are known to have good "knockdown" activity, and are therefore particularly useful in household sprays for flying insects. Such compounds, when combined with Resmethrin and, preferably, a synergist such as piperonyl butoxide, produce a useful, general purpose House and Garden-type aerosol with good knockdown and killing power. Such compositions would be expected to have a greater general acceptance if the odor problems associated with Resmethrin could be overcome.

OBJECTS OF THE PRESENT INVENTION

It is an object of the present invention to improve the acceptability of 5-benzyl-3-furylmethyl chrysanthemate as a broad spectrum insecticide.

It is a further object of the present invention to improve the acceptability of 5-benzyl-3-furylmethyl chrysanthemate as a component in general purpose insecticide compositions.

It is a still further object of the present invention to stabilize pesticidal compositions containing 5-benzyl-3-furylmethyl chrysanthemate to prevent the formation of unpleasant odor.

The other objects, features and advantages of the present invention will become more apparent in light of the following detailed description of the preferred embodiment thereof.

According to one embodiment of the present invention, there is provided a substantially odor-free, oil-based pesticidal composition comprising, in combination, a pesticidal component having as the active pesticidal agent (5-Benzyl-3-furyl)methyl 2,2-dimethyl-3-(2-methylpropenyl)cyclopropanecarboxylate, and a stabilizing component comprising at least one compound selected from the group consisting of lionlenic acid oils, tall oils and tung oils having conjugated double bonds, wherein the proportion of said stabilizing component present is at least two (2) times the proportion of the (5-Benzyl-3-furyl)methyl 2,2-dimethyl-3-(2-methylpropenyl)cyclopropanecarboxylate.

According to another embodiment of the present invention, there is provided a substantially odor-free, oil-based pesticidal composition comprising, in combination, a pesticidal component having at least two active pesticidal agents, one of which agents is (5-Benzyl-3-furyl)methyl 2,2-dimethyl-3-(2-methylpropenyl)cyclopropanecarboxylate, and a stabilizing component comprising at least one compound selected from the group consisting of linolenic acid oils, tall oils and tung oils having conjugated double bonds wherein the proportion of said stabilizing component present is at least two (2) times the proportion of (5-Benzyl-3-furyl)methyl 2,2-dimethyl-3-(2-methylpropenyl)cyclopropanecarboxylate.

DETAILED DESCRIPTION OF THE PRESENT INVENTION

This application is related to another, filed contemporaneously herewith, and having a common assignee. The compositions disclosed in both applications employ the pesticidal agent (5-Benzyl-3-furyl)methyl 2,2-diemthyl-3-(2-methylpropenyl)cyclopropanecarboxylate. As noted above, this compound is sometimes written as 5-benzyl-3-furylmethylchrysanthemate, but is more generally known by the generic term Resmethrin.

Resmethrin is soluble in various organic solvents, but insoluble in water. It is commonly sold as a 40% concentrate in an aromatic solvent. Solvents normally employed for this purpose include those commercially available from the Amoco Chemical Co. under the registered trademark "Panasol AN-2", from the Tenneco Oil Co. under the register trademark "Tenneco 500-100", and from Exxon Inc. under the registered trademark "Aromatic 150". These compositions may then be further diluted and pressurized to produce oil-based aerosols which may be intended for numerous applications of a sporodic nature, or a single complete discharge.

As noted above, the unpleasant odor produced by Resmethrin is readily detected after exposure to sunlight or bright artificial light. Studies of degradation products of Resmethrin have shown that one of the minor photo-decomposition products is phenylacetic acid. Additional studies have shown that it is the presence of this compound which accounts for the unpleasant, urine-like odor. Only a small amount of phenylacetic acid is produced in the decomposition of Resmethrin. However, organoleptic testing procedures have shown that as little as one part per trillion of phenylacetic acid in the air can be detected by odor panels. Obviously, to avoid the unpleasant odor, prevention of the formation of phenylacetic acid must be substantially complete.

In the study of the degradation of Resmethrin, it was noticed that when Resmethrin formulations are sprayed on glass plates the Resmethrin appears to crystallize before the unpleasant odor typical of phenylacetic acid begins to appear. It was then proposed that the phenylacetic acid odor might be prevented by the addition of some non-volatile liquid to the volatile carrier which would prevent such crystal formation. Emulsifiers, mineral oils, corrosion inhibitors and vegetable oils were proposed and tested for this purpose. However, the only additives tested which consistently prevented the formation of the unpleasant odor of Resmethrin were wheat germ oils, soybean oil, linseed oil, tung oil and some tall oils. When these results were further examined, it became apparent that the additives which were operative as stabilizers were linolenic acid oils, tall oils and tung oils having conjugated double bonds. Such stabilizers were required to be present in an amount of at least two (2) times the proportion of Resmethrin in order to be effective for a satisfactory period of time. Any amount of stabilizer above this minimum will have the effect of further preventing the formation of the unpleasant odor typical of phenylacetic acid. However, it is not seen that the amount of such stabilizer will ever need to exceed fifty (50) times the proportion of Resmethrin in the practice of this invention as a practical matter. In sprays formulated for numerous applications, the amount of stabilizer will be on the order of three to five times the amount of Resmethrin. For total release sprays, requiring a single complete discharge, it has been found preferable to employ a much larger proportion, on the order of twenty to forty times the amount of Resmethrin.

Although Resmethrin is an excellent broad spectrum insecticide, it is known to lack the quick "knockdown" properties required in a household spray for flying insects. As noted earlier, synthetic pyrethroids, varously known as Bioallethrin, Allethrin, Neopynamin, and other pyrethrins are all known to have such "knockdown" characteristics. The combination of any of these compounds with Resmethrin, preferably with a synergist such as piperonyl butoxide, will produce a general purpose House and Garden-type spray having good knock-down and kill. Further, the present invention will provide the benefits of such a spray without the problems associated with the unpleasant odor caused by the phenylacetic acid which is created when Resmethrin begins to photo-decompose. This is accomplished in the same manner.

The present invention is shown more clearly in the following illustrative examples.

EXAMPLE 1

Seven and one-half grams (7.5 g.) of a 40% Resmethrin concentrate in a commercially available aromatic solvent, representing three grams (3.0 g.) of Resmethrin, and fifteen grams (15.0 g.) of wheat germ oil, obtained commercially from the Sanrak Corp. were dissolved in a sufficient quantity of deodorized kerosene to make up a total weight of one hundred grams (100 g.). This solution was then hand pumped onto glass plates which were subsequently exposed to bright sunlight. After several hours the plates were examined and the unpleasant odor of phenylacetic acid was not detected. Glass plates sprayed with a control solution formulated in the same manner, but without the wheat germ oil, produced the strong, unpleasant, urine-like odor typical of phenylacetic acid within several hours.

EXAMPLE 2

One-half gram (0.5 g.) of the same 40% Resmethrin concentrate employed in Example 1, representing two-tenths of a gram (0.2 g.) of Resmethrin, one-tenth of a gram (0.1 g.) of Bioallethrin, a synthetic pyrethroid commercially available from Roussell Uclaf, and four grams (4.0 g.) of refined edible soybean oil were dissolved in a sufficient quantity of deodorized kerosene to make a total weight of twenty grams (20.0 g.). This solution was introduced into an aerosol container and a valve was attached. The container was then charged with eighty grams (80.0 g.) of a 1:1 mixture of Freon 11 and Freon 12, both commercially available fluorocarbons from E.I. du Pont de Nemours. None of the unpleasant odor typical of phenylacetic acid was detected on glass plates which were sprayed with the aerosol composition and exposed to bright sunlight on a windowsill. Glass plates sprayed with a control aerosol formulated in the same manner, but without the soybean oil, produced the strong, unpleasant, urine-like odor typical of phenylacetic acid within several hours.

EXAMPLE 3

Twenty-five one-hundredths of a gram (0.25 g.) of the same 40% Resmethrin concentrate employed in the previous examples, representing one-tenth of a gram (0.1 g.) of Resmethrin and two grams (2.0 g.) of commercial grade tung oil commercially available from the Welch, Holme & Clark Company, were dissolved in a sufficient quantity of deodorized kerosene to make up a total weight of ninety-seven grams (97.0 g.). This solution was introduced into an aerosol container and a valve was attached. The container was then charged with three grams (3.0 g.) of carbon dioxide to bring the container pressure to one hundred pounds per square inch gauge (100 psig).

None of the unpleasant odor typical of phenylacetic acid was detected on carpet pieces which were sprayed with the aerosol composition and exposed to bright sunlight. Carpet pieces sprayed with a control aerosol formulated in the same manner, but without the tung oil, produced the strong, unpleasant, urine-like odor typical of phenylacetic acid within several hours.

EXAMPLE 4

One gram (1.0 g.) of the same 40% Resmethrin concentrate employed in the previous examples, representing four-tenths of a gram (0.4 g.) of Resmethrin, twenty grams (20.0 g.) of tall oil, available commercially from Arizona Chemical Co. under the registered trademark "Actinol FA-1", and nine grams (9.0 g.) of deodorized kerosene were dissolved in a sufficient quantity of methylene chloride to make up a total weight of 75 grams. This solution was introduced into an aerosol container and a valve was attached. The container was then charged with twenty-five grams (25.0 g.) of commercial grade propane to provide an aerosol spray which would deliver one hundred milligrams (100 mg.) of spray composition every thirty seconds for thirty days.

This aerosol was allowed to disperse in a twelve foot (12 ft.) by twelve foot (12 ft.) room for several days. None of the unpleasant odor typical of phenylacetic acid was detected. A similar test was conducted with a control aerosol formulated in the same manner, but without the tall oil, and the strong, unpleasant, urine-like odor typical of phenylacetic acid was produced within several hours.

The other features, advantages and specific embodiments of this invention will become readily apparent to those exercising ordinary skill in the art after reading the foregoing disclosures. These specific embodiments are within the scope of the claimed subject matter unless otherwise expressly indicated to the contrary. Moreover, while specific embodiments of this invention have been described in considerable detail, variations and modifications of these embodiments can be effected without departing from the spirit and scope of this invention as disclosed and claimed.

What is claimed is:

1. An odor-free, oil-based insecticidal composition comprising, in combination, an insecticidal component having as the active insecticidal agent (5-Benzyl-3-furyl)-methyl 2,2-dimethyl-3-(2-methylpropenyl)-cyclopropanecarboxylate in an aromatic solvent, and a stabilizing component comprising at least one compound selected from the group consisting of linolenic acid oils, tall oils and tung oils having conjugated double bonds, wherein the proportion of said stabilizing component present is at least two (2) times the proportion of the (5-Benzyl-3-furyl)-methyl 2,2-dimethyl-3-(2-methylpropenyl)-cyclopropanecarboxylate present.

2. The insecticidal composition of claim 1 in which the proportion of said stabilizing component present is from two (2) to fifty (50) times the proportion of (5-Benzyl-3-furyl)-methyl 2,2-dimethyl-3-(2-methylpropenyl)-cyclopropanecarboxylate.

3. The insecticidal composition of claim 1 in which the proportion of said stabilizing component present is from three (3) to five (5) times the proportion of (5-Benzyl-3-furyl)-methyl 2,2-dimethyl-3-(2-methylpropenyl)-cyclopropanecarboxylate.

4. The insecticidal composition of claim 1 in which the proportion of said stabilizing component present is from twenty (20) to forty (40) times the proportion of (5-Benzyl-3-furyl)-methyl 2,2-dimethyl-3-(2-methylpropenyl)-cyclopropanecarboxylate.

5. An odor-free, oil-based insecticidal composition comprising, in combination, an insecticidal component having at least two active insecticidal agents, one of which agents is (5-Benzyl-3-furyl)-methyl 2,2-dimethyl-3-(2-methylpropenyl)-cyclopropanecarboxylate and the second of which is a second synthetic pyrethroid having a good knockdown effect in an aromatic solvent, and a stabilizing component comprising at least one compound selected from the group consisting of linolenic acid oils, tall oils and tung oils having conjugated double bonds, wherein the proportion of said stabilizing component present is at least two (2) times the proportion of (5-Benzyl-3-furtyl)-methyl 2,2-dimethyl-3-(2-methylpropenyl)-cyclopropanecarboxylate present.

* * * * *

UNITED STATES PATENT AND TRADEMARK OFFICE
CERTIFICATE OF CORRECTION

PATENT NO. : 4,677,117
DATED : June 30, 1987
INVENTOR(S) : JOSEPH B. HAUS

It is certified that error appears in the above-identified patent and that said Letters Patent is hereby corrected as shown below:

ON THE TITLE PAGE,

[73]   "Roussel Uclaf, Paris France" should be

--Bio Uclaf Corp.
   Wilmington, De. --.

Signed and Sealed this

Twenty-fourth Day of November, 1987

Attest:

DONALD J. QUIGG

Attesting Officer

Commissioner of Patents and Trademarks